United States Patent [19]

Stephens et al.

[11] Patent Number: 5,197,955
[45] Date of Patent: Mar. 30, 1993

[54] UNIVERSAL SEAL FOR TROCAR ASSEMBLY

[75] Inventors: Randy R. Stephens, Fairfield, Ohio; John M. Collins, Ipswich; Robert Farra, Leominster; Dean Pichon, Concord, both of Mass.

[73] Assignee: Ethicon, Inc., N.J.

[21] Appl. No.: 781,026

[22] Filed: Oct. 18, 1991

[51] Int. Cl.⁵ .............................................. A61M 29/02
[52] U.S. Cl. ...................................... 604/167; 604/256
[58] Field of Search ............... 604/164, 167, 169, 248, 604/256

[56] References Cited

U.S. PATENT DOCUMENTS

| | | | |
|---|---|---|---|
| 4,535,773 | 8/1985 | Yoon | 604/51 |
| 4,540,411 | 9/1985 | Bodicky | 604/169 |
| 4,613,329 | 9/1986 | Bodicky | 604/163 |
| 4,654,030 | 3/1987 | Moll et al. | 604/165 |
| 4,909,798 | 3/1990 | Fleischhacker et al. | 604/167 |
| 4,978,341 | 12/1990 | Niederhauser | 604/167 |
| 5,030,206 | 7/1991 | Lander | 604/164 |
| 5,053,016 | 10/1991 | Lander | 604/169 |
| 5,059,186 | 10/1991 | Yamamoto et al. | 604/167 |
| 5,108,380 | 4/1992 | Herlitze et al. | 604/169 |

Primary Examiner—John D. Yasko
Assistant Examiner—Anthony Gutowski
Attorney, Agent, or Firm—Dressler, Goldsmith, Shore, Sutker & Milnamonw, Ltd.

[57] ABSTRACT

Trocar assembly devices are disclosed that include an improved seal assembly that accommodates instruments having a wide range of diameters. The seal assembly includes a universal seal member that is generally of hourglass shape defining converging and diverging side walls that form a constricted center bore portion therebetween. Various alternative means are provided to either increase or decrease the inner diameter of the center bore portion of the seal member.

26 Claims, 6 Drawing Sheets

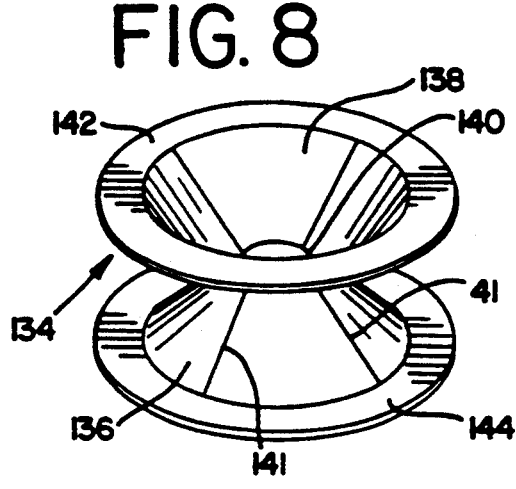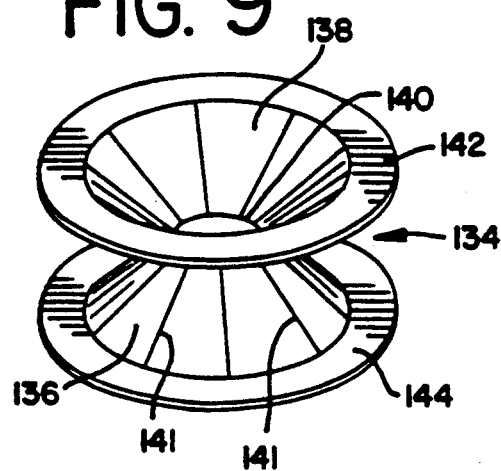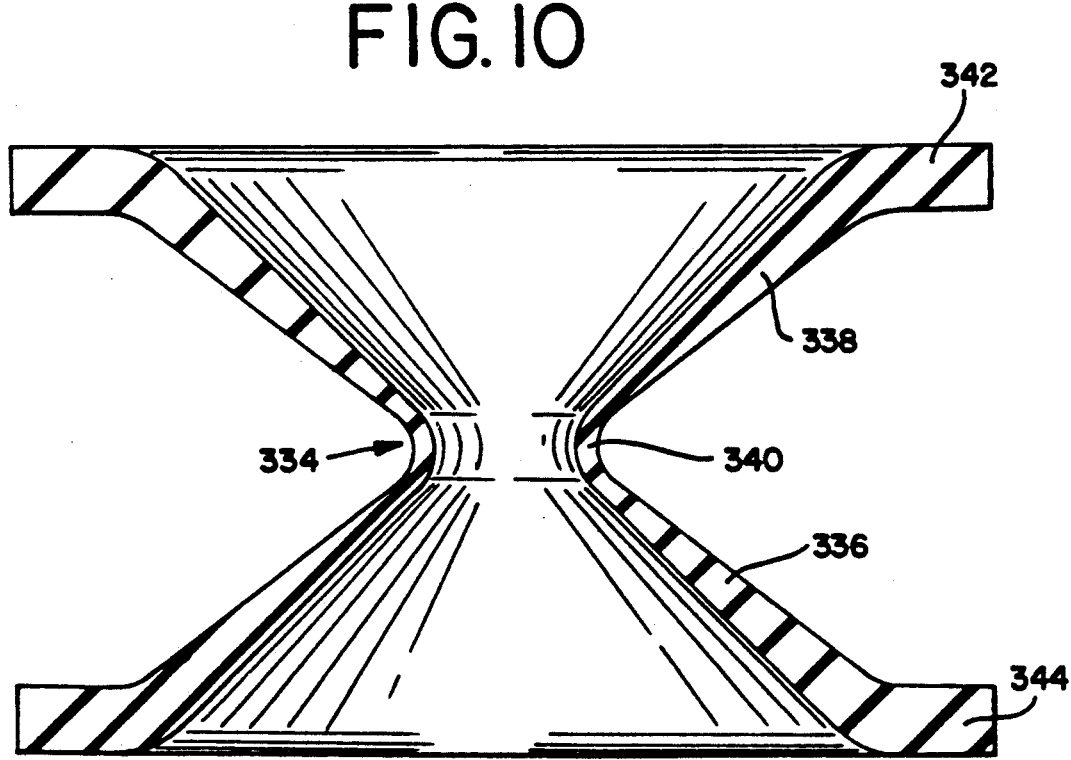

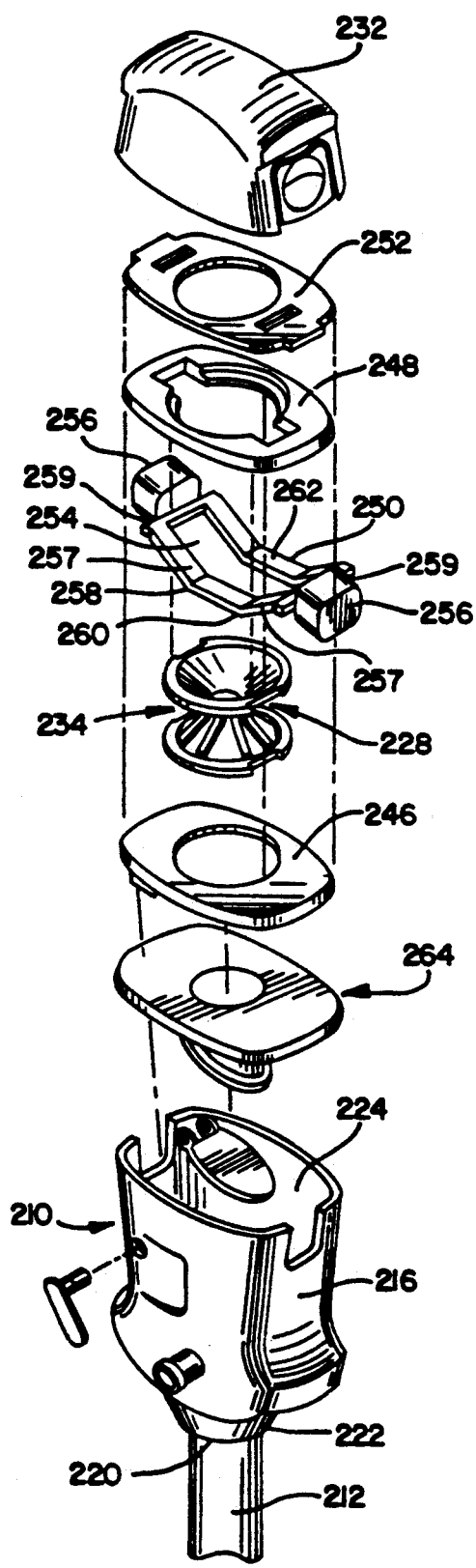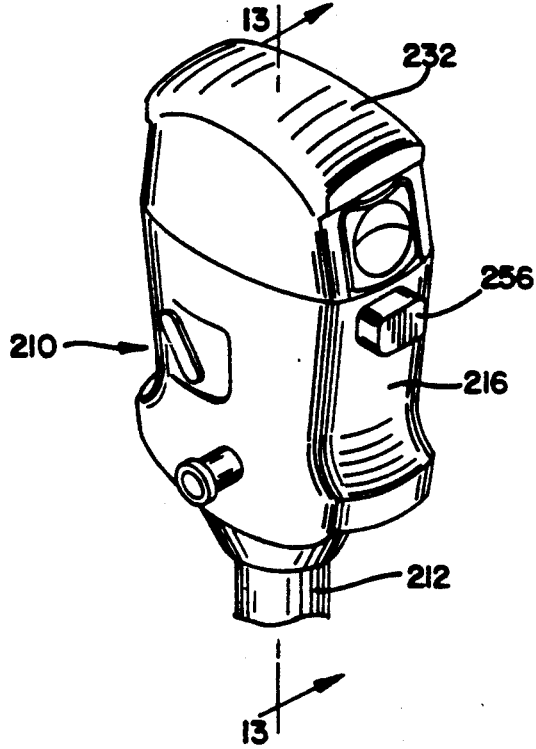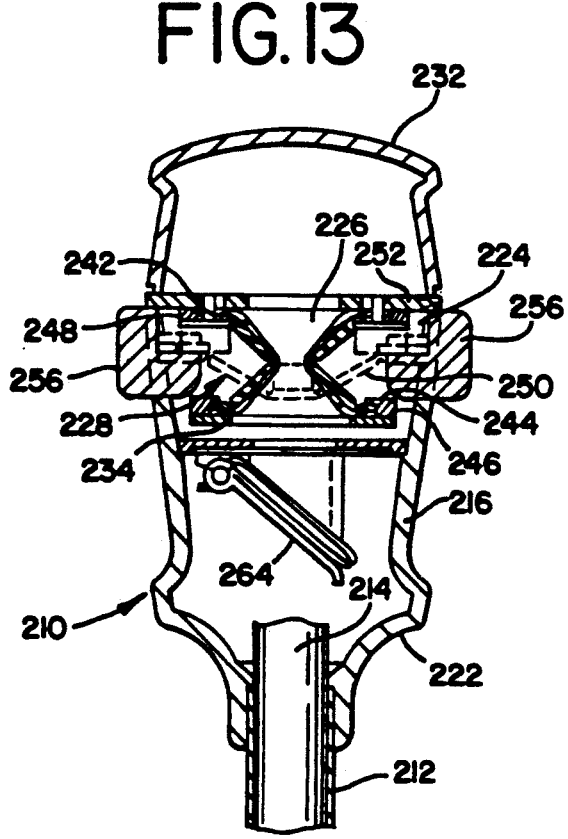

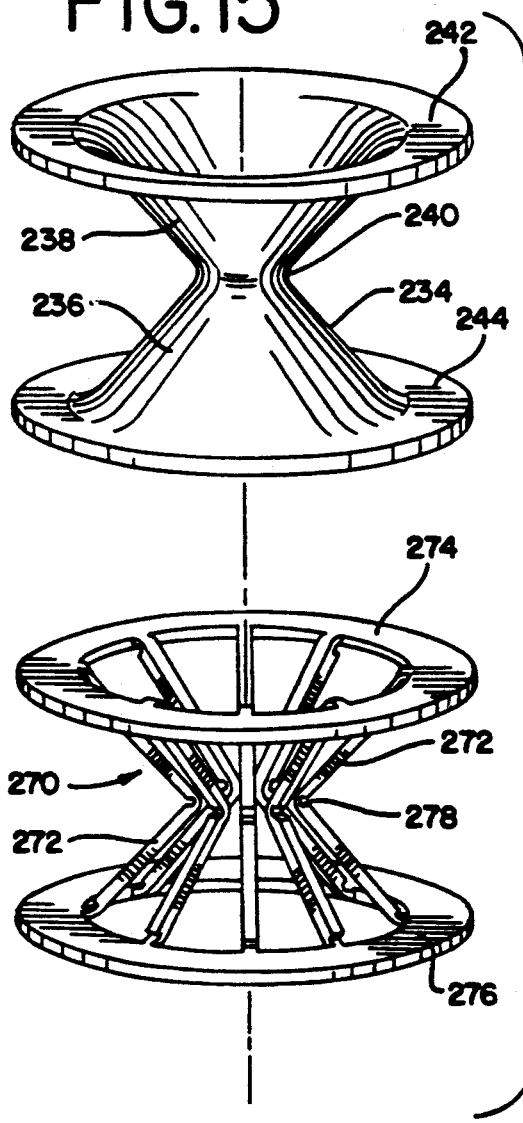
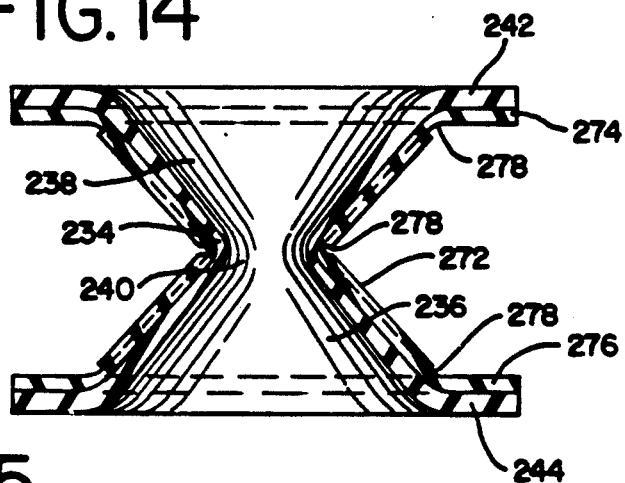
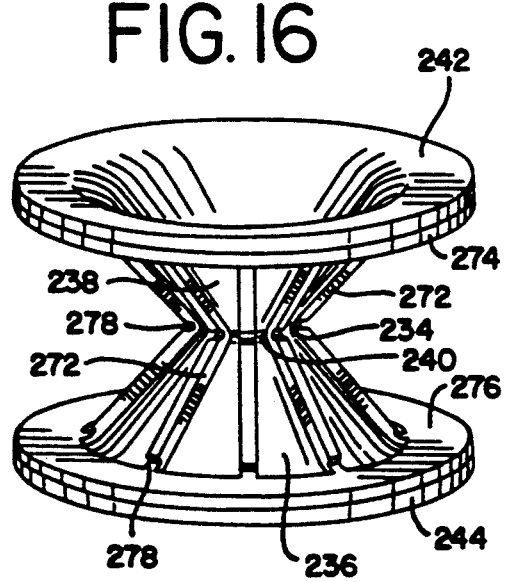

UNIVERSAL SEAL FOR TROCAR ASSEMBLY

FIELD OF THE INVENTION

This invention generally relates to surgical instruments; and more particularly, the invention relates to trocar assembly devices for providing communication into an anatomical cavity. Trocar assembly devices in accordance with the present invention include an improved seal member able to accommodate instruments and tools having a wide range of diameters.

BACKGROUND OF THE INVENTION

A trocar assembly is a surgical instrument that is used to gain access to a body cavity. A trocar assembly generally comprises two major components, a trocar tube and an obturator. The trocar tube is inserted through the skin to access a body cavity through the tube in which laparoscopic or arthroscopic surgery and endoscopic procedures are to be performed. In order to penetrate the skin, the distal end of the trocar tube is placed against the skin and an obturator is inserted through the tube. The obturator has a sharp point or cutting edge at its distal end. By applying pressure against the proximal end of the obturator, the sharp point is forced through the skin until it enters the body cavity. The trocar tube is inserted through the perforation made by the obturator and the obturator is withdrawn, leaving the trocar tube as an accessway to the body cavity. Examples of trocar assembly devices are disclosed in U.S. Pat. No. 4,535,773.

The proximal end portion of the trocar tube is typically adjoined by a housing that defines a chamber having an open distal end portion that communicates with the interior lumen defined by the trocar tube. An obturator and other surgical implements or tools axially extend into and are withdrawn from the trocar tube through the distal end portion of the chamber. It is the present practice to provide the chamber with a sealing means, such as a sealing grommet or gasket, through which the obturator or other implements extend. The sealing means seals against the outer surface of the inserted implement and thereby prevents fluids from leaving or entering the body cavity through the trocar tube. The range over which current sealing means effectively operate to seal against implements of different outside diameters is approximately ±1 mm. Accordingly, it is frequently necessary to utilize different size trocar tubes during a medical procedure to accommodate implements and tools of different diameters.

There is a need for a trocar assembly that includes a sealing means that is compatible with the expanding number of different size implements and tools that are required during a medical procedure. The typical range of the outside diameter of such implements and tools is from about 2 mm to about 12 mm. A trocar assembly that covers this size range of implements would minimize surgeon adjustments, saving time and reducing the number of trocar tubes required during a medical procedure.

It is also desirable for the sealing means to function during off-center insertion of an implement having sharp edges, such as clip appliers, or when an implement is moved radially after insertion. It is further desirable that the sealing means facilitate the insertion or removal of implements and the removal of tissue therethrough.

SUMMARY OF THE INVENTION

In accordance with the principles of the present invention, trocar assembly devices are provided that include a universal seal member that accommodates tools of various diameters without losing fluids from the anatomical cavity. The seal member is generally of an hourglass shape, defining generally converging and diverging side walls that form a constricted center bore portion therebetween.

In accordance with a first preferred embodiment of the invention, the center bore portion preferably has a diameter of about 6 mm to permit the insertion of implements, such as clip appliers and the like, therethrough without piercing the seal member. To accommodate a tool having a diameter in excess of 6 mm, the center bore portion is stretched as the tool is inserted therethrough. In order to accommodate tools having a diameter less than 6 mm, means is provided to compress or constrict the center bore portion.

The invention contemplates the utilization of alternative means to selectively compress the center bore portion of the seal member. In accordance with one embodiment, a twisting force is applied to the seal member and a force is applied to separate the respective ends of the seal member. In accordance with a further embodiment, a spring member applies pressure to an outer surface of the center bore portion. In accordance with another embodiment of the invention a positive gas or liquid pressure is applied to the outside surface of the seal member.

In accordance with second and third preferred embodiments of the invention, the center bore portion is sized to provide a lip seal around the smallest diameter tool (about 4 mm) and is allowed to enlarge to accommodate the larger diameter tools (about 12 mm).

The invention contemplates the utilization of alternative means to selectively enlarge the diameter of the center bore portion. In accordance with one embodiment, the seal member is designed so that the ratio of the axial deflection of the seal member to the change in diameter of the center bore portion is from about 1:3 to about 3:1 and most preferably about 1:1. This relationship may be achieved by using either tensile elements, such as Kevlar ® strings, or high durometer ribs located axially through or adjacent the side wall of the seal member. In accordance with another embodiment, a vacuum is applied to the outside surface of the seal member to create a differential pressure on the seal member causing the center bore portion to expand.

In accordance with a fourth preferred embodiment of the invention, the center bore portion has a diameter of about 7 mm and is provided with means to selectively increase and decrease the diameter of the center bore portion.

BRIEF DESCRIPTION OF THE DRAWINGS

A more complete appreciation of this invention, and many of the attendant advantages thereof, will be readily apparent as the same becomes better understood by reference to the following detailed description, when considered in conjunction with the accompanying drawings, in which like reference numerals indicate the same or similar components, wherein:

FIG. 8 is a perspective view of a seal member constructed in accordance with the invention;

FIG. 9 is a perspective view of a seal member constructed in accordance with the invention;

FIG. 10 is an enlarged cross-sectional view of a seal member constructed in accordance with the invention;

FIG. 11 is an exploded perspective view of a third preferred embodiment of a trocar assembly device incorporating a seal member assembly constructed in accordance with the invention;

FIG. 12 is a perspective view of the trocar assembly device shown in FIG. 11, with the obturator fully extended into the trocar tube;

FIG. 13 is a cross-sectional view taken along line 13—13 in FIG. 12;

FIG. 14 is a cross-sectional view of an alternative embodiment of a seal member constructed in accordance with the invention;

FIG. 15 is an exploded perspective view of the seal member shown in FIG. 14;

FIG. 16 is a perspective view of the seal member shown in FIG. 14; and

DETAILED DESCRIPTION OF PREFERRED EMBODIMENTS

Figure 1:
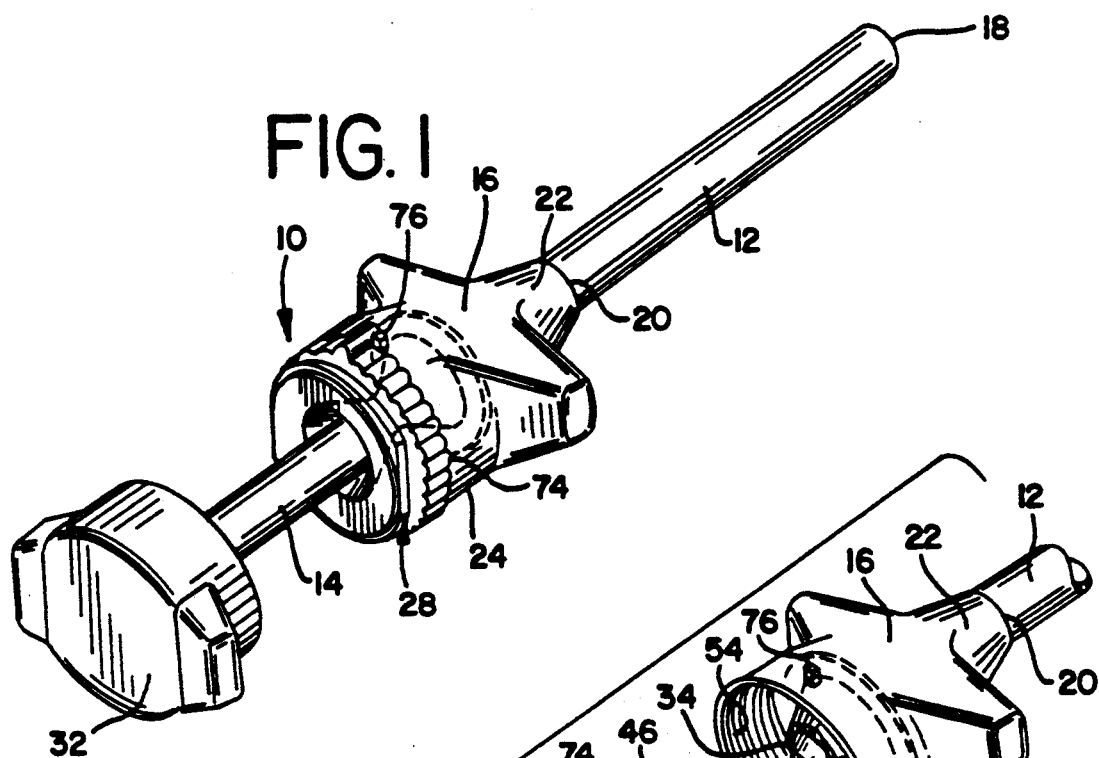
FIG. 1 is a perspective view of a first preferred embodiment of a trocar assembly device incorporating a seal member assembly constructed in accordance with the invention, with the obturator partially extended into the trocar tube.
Figure 2:
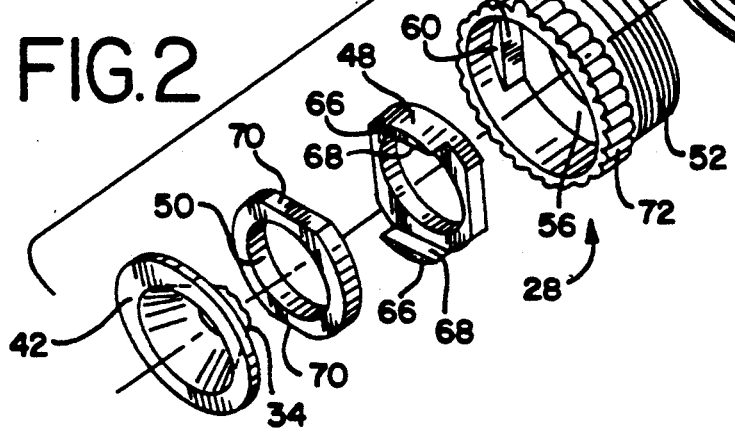
FIG. 2 is an exploded perspective view of a portion of the trocar assembly device shown in FIG. 1, showing the seal member assembly in accordance with the invention.

Referring to FIGS. 1 and 2, there is shown a first preferred embodiment of a trocar assembly device 10 that includes a seal member assembly 28 having a seal member 34 constructed in accordance with the invention. The particular construction of the trocar assembly device does not form a part of the invention and the brief disclosure thereof is merely for exemplary purposes.

Trocar assembly 10 includes a trocar tube 12, an obturator 14, and a housing or handle 16. Trocar tube 12 defines an interior lumen having an open distal end portion 18 and an open proximal end portion 20. Proximal end portion 20 extends into and is mounted in a distal end portion 22 of handle 16. Handle 16 has an open proximal end portion 24 that defines an opening 26. Opening 26 is provided with a seal member assembly 28 constructed in accordance with the present invention and described in detail hereinbelow.

An obturator 14 is slideably and removably extendable within trocar tube 12 and is inserted into handle 16 and trocar tube 12 through seal member assembly 28 and opening 26. An obturator handle 32 is provided at the proximal end of the obturator and a sharpened point or blade (not shown) is formed at the distal end thereof. As is well known in the art, seal member assembly 28 cooperates with obturator 14 or an implement extending through trocar tube 12 to sealingly engage the outer surface thereof and thereby preclude the passage of fluids through handle 16.

Figure 3:
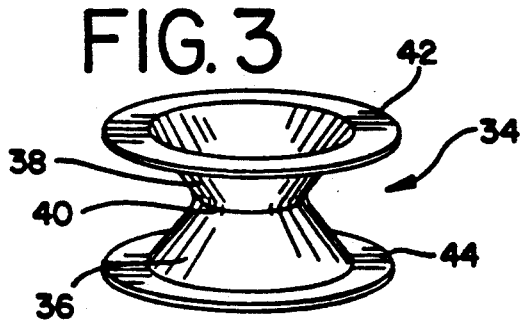
FIG. 3 is a perspective view of a seal member constructed in accordance with the invention.

Seal member assembly 28 includes a seal member 34 constructed in accordance with the present invention. Referring to FIG. 3, seal member 34 is generally of an hourglass shape defining generally converging and diverging side walls 36 and 38 that form a constricted center bore portion 40 at the intersection thereof. The outer edges of side walls 36 and 38 are respectively formed with an outer or top annular flange portion 42 and an inner or bottom annular flange portion 44 extending outwardly therefrom. In accordance with a preferred embodiment, the inner diameter of the center bore portion 40 is preferably equal to the width of sharp tips on instruments, currently from about 4.0 mm to about 10.0 mm and most preferably about 6.0 mm. The seal member is made from an elastomeric material such as silicon or Kraton® (a thermoplastic elastomeric A-B-A, styrene-isoprene-styrene, block copolymer manufactured by the Shell Chemical Company). The inner surface may be coated with a lubricant, such as hydrogel material or silicon, etc., to minimize frictional forces while inserting or moving implements inside the trocar.

Seal member assembly 28 provides a means for selectively compressing or decreasing the inner diameter of center bore portion 40. Referring to FIG. 2, assembly 28 includes a seal retaining ring 46, a floating ring 48, and a top seal support ring 50. Retaining ring 46 is provided with an externally threaded distal portion 52 that is received by a cooperating internally threaded portion 54 formed in opening 26. An annular surface 56 having an opening 58 is formed in an intermediate portion of ring 46. A pair of opposing abutment portions 60 (only one of which is shown) extend proximally from surface 56 so as to define proximally extending parallel surfaces 62 within ring 46.

Floating ring 48 is positioned in ring 46 on surface 56. Ring 48 is formed with parallel surfaces 64 that slidingly engage surfaces 62 within ring 46. A pair of opposing abutment portions 66 extend from ring 48 so as to define proximally extending parallel surfaces 68. Ring 48 is dimensioned so as to permit limited sliding movement thereof within ring 46 between surfaces 62.

Support ring 50 is received between surfaces 68 of ring 48 within ring 46. Ring 50 is formed with parallel surfaces 70 that slidingly engage surfaces 68. Ring 50 is dimensioned so as to permit limited sliding movement thereof within ring 48 in a direction perpendicular to the direction of movement of ring 48 in ring 46.

Seal member 34 is mounted in assembly 28 such that the side walls 36 and 38 extend through rings 46, 48 and 50. The bottom flange 44 of the seal member 34 is suitably retained within handle 16 in a fixed manner at the distal end of ring 46. The top flange 42 of the seal member 34 is positioned adjacent to the outer surface of ring 50 and is movable therewith. Ring 46 is formed with an outer serrated portion 72 to facilitate the turning of ring member 46 in handle 16. A finger 74 is formed on the outer surface of ring 46 that cooperates with a detent 76 on the outside of handle 16 to limit the rotation of ring 46 to one revolution.

In operation, the trocar assembly 10 is typically received in a form wherein the seal member 34 is in its unstressed condition and wherein the center bore portion 40 has an inner diameter of about 6.0 mm. In this condition, the seal member 34 is able to seal against implements having outer diameters from about 7 mm to about 12 mm. When it is necessary to direct an implement having a diameter less than about 7.0 mm through trocar assembly 10, ring 46 is rotated causing the seal member to simultaneously twist and elongate. The twisting of the seal member causes it to form pleats that buckle towards the center bore portion 40 to effectively reduce the diameter of the center bore portion. The elongation of the seal member facilitates the sealing of the compressed center bore portion against an implement extending therethrough. Finger 74 contacts detent 76 to limit the rotational movement of ring 46 to one revolution and thereby controls the extent of twisting and elongation applied to the seal member.

Due to the size range of the implements to be directed through seal member 34, it is possible to direct implements through the seal member in a non-concentric manner. Non-concentrically located implements tend to cause leaks due to the internal stresses in the seal member pulling toward the center and away from the implement. This problem is alleviated by permitting one end of the seal member to float while the other end of the seal member is anchored. The relative sliding movement of rings 48 and 50 causes the top flange portion 42 of seal member 34 to float and thereby permits the center bore portion 40 to move radially with minimal internal stresses generated on the seal member. The converging and diverging side walls 36 and 38 facilitate the insertion of implements and the removal of tissue through the seal member.

Figure 4:
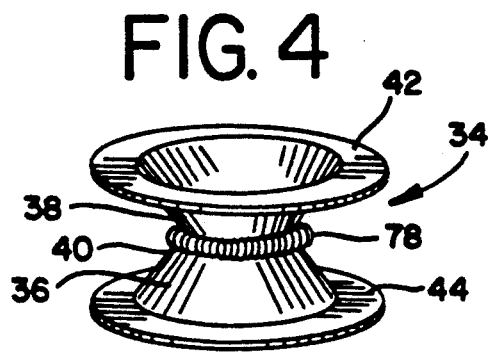
FIG. 4 is a perspective view of a seal member in accordance with an alternative embodiment of the invention.

Referring to FIG. 4, an alternative means is provided for decreasing the inner diameter of center bore portion 40 of seal member 34. A low rate, higher elongation spring member 78 is applied around the center bore portion 40 to provide a compressive force to the center bore portion without applying an undue additional force when a large diameter implement is directed through the seal member. Spring member 78 may include various configurations of elastomers, such as rubber bands or an additional hourglass, and metal springs.

It is further contemplated that the inner diameter of the center bore may be compressed by applying a positive pressure to the outside surface of the seal member that causes the hourglass shape to collapse toward the center line. The amount of pressure applied varies with the material and thickness of the seal member. For example, a seal member made of silicon and having a wall thickness of 0.02 inches, requires a pressure of about 1 psi. Although not shown in the drawings, the pressure may be applied through a port that communicates with a sealed chamber in the handle that houses the seal member. A suitable source of fluid pressure may be directed through the port.

Figure 6:
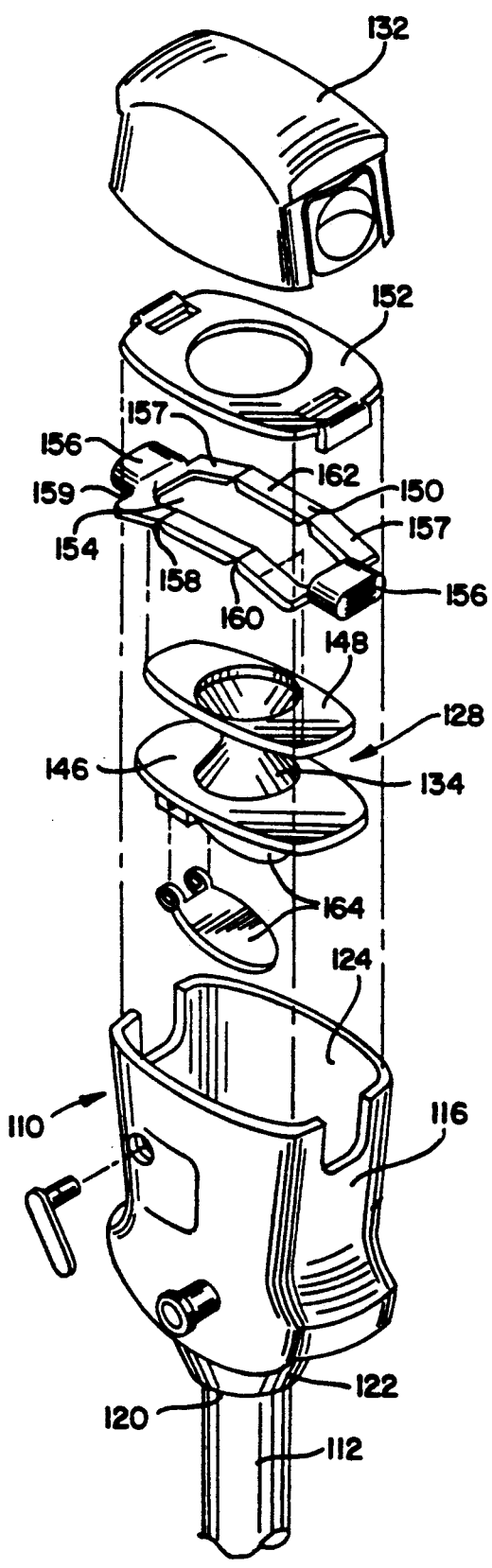
FIG. 6 is an exploded perspective view of the trocar assembly device shown in FIG. 5 showing a seal member assembly in accordance with the invention.
Figure 5:
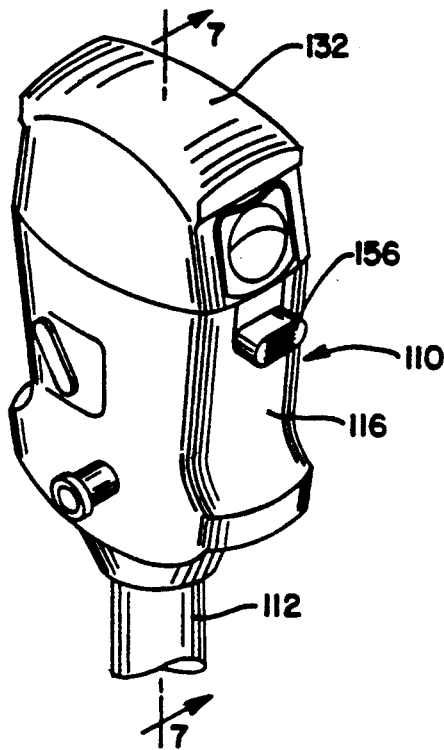
FIG. 5 is a perspective view of a second preferred embodiment of a trocar assembly device incorporating a seal member assembly constructed in accordance with the invention, with the obturator fully extended into the trocar tube.
Figure 7:
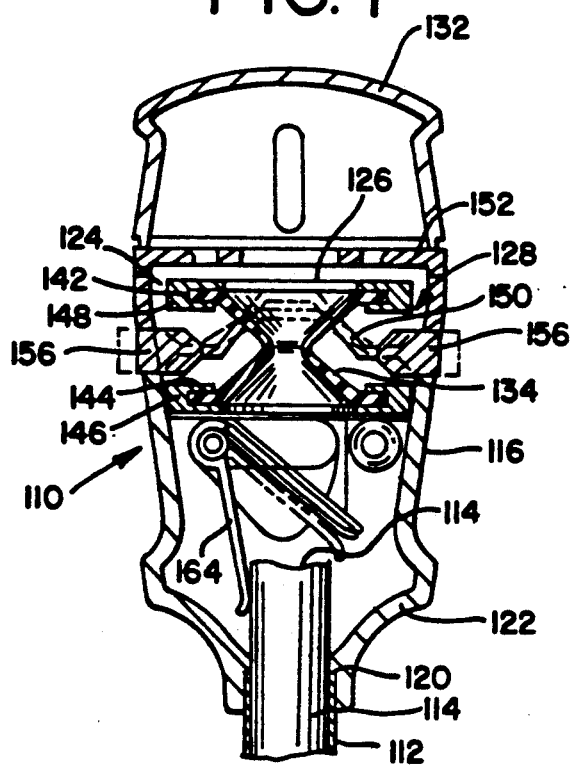
FIG. 7 is a cross-sectional view taken along line 7—7 in FIG. 5.

Referring to FIGS. 5-7, there is shown a second preferred embodiment of a trocar assembly device 110 that includes a seal assembly 128 having a seal member 134 constructed in accordance with an alternative embodiment of the invention. Trocar assembly 110 includes a trocar tube 112, an obturator 114, and a housing or handle 116. Trocar tube 112 defines an interior lumen having an open distal end portion (not shown) and an open proximal end portion 120. Proximal end portion 120 extends into and is mounted in a distal end portion 122 of handle 116. Handle 116 has an open proximal end portion 124 that defines an opening 126. Opening 126 is provided with a seal member assembly 128 constructed in accordance with an alternative embodiment of the invention.

An obturator 114 is slidably and removably extendable within trocar tube 112 and is inserted into handle 116 and trocar tube 112 through seal member assembly 128 and opening 126. An obturator handle 132 is provided at the proximal end of the obturator. Seal member assembly 128 cooperates with obturator 114 or an implement extending through trocar tube 112 to sealingly engage the outer surface thereof and thereby preclude the passage of fluids through handle 116.

Seal member assembly 128 includes a seal member 134 constructed in accordance with the invention, Referring to FIGS. 8 and 9, seal member 134 is generally of the same hourglass configuration discussed above with respect to seal member 134. Seal member 134 includes converging and diverging side walls 136 and 138 that form a constricted center bore portion 140 at the intersection thereof. The outer edges of side walls 136 and 138 respectively have an outer or top annular flange portion 142 and inner or a bottom annular flange portion 144 extending outwardly therefrom. In accordance with a preferred embodiment, the inner diameter of the center bore portion 140 is preferably from about 1.0 mm to about 5.0 mm and most preferably about 4.0 mm. The inner diameter is selected to seal around the smallest diameter implement that is contemplated to be directed through the seal member.

For reasons that will hereinbelow become more apparent, seal member 134 is designed so that the ratio of the axial deflection of the seal member to the change in diameter of the center bore portion is from about 1:3 to about 3:1 and most preferably about 1:1. In so doing, when the seal member is stretched or elongated in the axial direction, the diameter of the center bore portion 140 increases a like amount. The above relationship may be achieved by using tensile elements, such as strings or high durometer ribs placed axially through the walls of the seal member. These tensile elements or ribs are indicated by the reference numeral 141. The number of elements or ribs 141 may vary from about 3 to about 12 depending upon the shape of the expanded bore desired and the amount of radial elongation that may occur. The embodiment shown in FIG. 8 has four elements or ribs and the embodiment shown in FIG. 9 has twelve elements or ribs. In accordance with a preferred embodiment, eight spaced apart Kevlar ® strings are provided to achieve a desired ratio between the axial and radial deflection of the seal member.

Seal member assembly 128 provides a means for selectively expanding the inner diameter of center bore portion 140. Referring to FIGS. 6 and 7, assembly 128 includes a bottom seal collar 146, a seal member 134, a top seal collar 148, a seal expander member 150 and a top retainer member 152. The bottom flange 144 and the top flange 142 are respectively received and suitably retained in recesses formed in collars 146 and 148. Bottom seal collar 146 is fixed to the inside of housing 116 and thereby precludes axial movement of flange portion 144 of the seal member. Top seal collar 148 is positioned within housing 116 adjacent opening 126 in a manner that permits it to move or float toward and away from bottom seal collar 146. Such movement is effective to elongate or stretch the seal member and thereby increase the inner diameter of the center bore portion 140.

The axial movement of the top seal collar 148 is controlled by the seal expander member 150. Member 150 is generally rectangular member having a rectangular opening 154 formed therein. A pair of opposing fingers 156 extend outwardly from end portions 157 of member 150. The expander member is positioned in housing 116 with the seal member 134 extending through opening 154 and the fingers 156 extending through cooperating openings in housing 116. The expander member is formed with living hinge portions 158, 159 and 160 so that squeezing of fingers 156 towards each other causes a center portion 162 to deflect upwardly and apply a force against the under surface of top seal collar 148 and further separate it and flange 142 from bottom seal collar 146 and flange 144.

Top retainer member 152 is attached to the upper end of housing 116 and is provided with openings to receive suitable attachment means associated with the obturator handle 132. As is well known in the art, trocar assembly 110 includes a flapper valve assembly 164 that is located in housing 116 immediately below bottom collar member 146.

In operation, the trocar assembly 110 is typically received in a form wherein the seal member 134 is in its unstressed condition and wherein the center bore portion has an inner diameter of about 4.0 mm. In this condition, the seal member 134 is able to seal against implements having outer diameters from about 5.0 mm to about 12.0 mm. When it is necessary to direct an implement having sharp tips, spaced greater than about 6.0 mm, through the trocar assembly 110 or to remove delicate tissue, fingers 156 are squeezed toward each other causing the center portion 162 of seal expander member 150 to deflect upwardly. The upward movement of portion 162 causes top seal collar 148 to further separate from bottom seal collar 146 and thereby elongate or stretch seal member 134. The elongation of seal member 134 causes the inner diameter of center bore 140 to increase and thereby facilitate the insertion of sharp implements therethrough. The floating of top seal collar 148 compensates for non-concentrically located implements in a similar manner as discussed above with respect to the embodiment shown in FIGS. 1-3.

It is also contemplated that the inner diameter of the center bore may be enlarged by applying a vacuum or negative pressure on the outside surface of the seal member to cause the hourglass shape to move outward from the center line. The amount of vacuum applied varies with the material and thickness of the seal member. Although not shown in the drawings, the vacuum may be applied through a port that communicates with a sealed chamber in the handle that houses the seal member. A suitable vacuum source may be connected to the port.

Referring to FIGS. 11-16, there is shown a third preferred embodiment of a trocar assembly device 210 that includes a seal assembly 228 having a seal member 234 constructed in accordance with an alternative embodiment of the invention. Trocar assembly 210 includes a trocar tube 212, an obturator 214 and a housing or handle 216. Trocar tube 212 defines an interior lumen having an open distal end portion (not shown) and an open proximal end portion 220. Proximal end portion 220 extends into and is mounted in a distal end portion 222 of handle 216. Handle 216 has an open proximal end portion 224 that defines an opening 226. Opening 226 is provided with a seal member assembly 228 constructed in accordance with an alternative embodiment of the invention.

An obturator 214 is slidably and removably extendable within trocar tube 212 and is inserted into handle 216 and trocar tube 212 through seal member assembly 228 and opening 226. An obturator handle 232 is provided at the proximal end of the obturator. Seal member assembly 228 cooperates with obturator 214 or an implement extending through trocar tube 212 to sealingly engage the outer surface thereof and thereby preclude the passage of fluids through handle 216.

Seal member assembly 228 includes a seal member 234 constructed in accordance with the invention, Referring to FIGS. 14-16, seal member 234 is generally of the same hourglass configuration discussed above with respect to seal members 34 and 134. Seal member 234 includes converging and diverging side walls 236 and 238 that form a constricted center bore portion 240 at the intersection thereof. The outer edges of side walls 236 and 238 respectively have an outer or top annular flange portion 242 and an inner or a bottom annular flange portion 244 extending outwardly therefrom. In accordance with a preferred embodiment, the inner diameter of the center bore portion 240 is preferably from about 1.0 mm to about 5.0 mm and most preferably about 4.0 mm. The inner diameter is selected to seal around the smallest diameter implement that is contemplated to be directed through the seal member.

For the same reasons discussed above with respect to trocar assembly 110, seal member 234 is designed so that the ratio of the axial deflection of the seal member to the change in diameter of the center bore portion is from about 1:3 to about 3:1 and most preferably about 1:1. In so doing, when the seal member is stretched or elongated in the axial direction, the diameter of the center bore portion 240 increases a like amount. In accordance with this embodiment of the invention, the above mentioned relationship may be achieved by providing a rib cage member 270 that is configurated to receive seal member 234 therein. Cage member 270 includes a plurality of spaced apart axially extending ribs 272 that conform to the converging and diverging side walls of the seal member. The ribs extend between an outer or top annular flange portion 274 and an inner or bottom annular flange portion 276, which flange portions cooperate with corresponding flange portions 242 and 244 associated with the seal member. The ribs are formed with living hinge portions 278 at the top, center and bottom portions thereof to permit them to flex and conform to the shape of the seal member as it is stretched. The number of ribs 272 may vary from about 3 to about 12, preferably about 8, depending upon the shape of the expanded bore desired and the amount of radial elongation that may occur.

As best seen in FIGS. 14 and 16, cage member 270 is received about and conforms to seal member 234. In accordance with a preferred embodiment, the seal member is molded over the cage member to form an integral assembly. The seal member 234 may be made from an elastomeric material such as silicon, Kraton, a blend of Kraton and polypropylene, or the like. The cage member 270 may be made from a plastic material such as Kraton, a blend of Kraton and polypropylene, or the like.

Seal member assembly 228 provides an alternative means for selectively expanding the inner diameter of center bore portion 240. Referring to FIGS. 11-13, assembly 228 includes a bottom seal collar 246, a seal member 234, a top seal collar 248, a seal expander member 250 and a top retainer member 252. The top flanges 242 and 274 and the bottom flanges 244 and 276 are respectively received and retained in recesses formed in collars 248 and 246 in a suitable manner. Top seal collar 248 is fixed to an upper portion of the inside of the chamber defined in housing 216 and thereby precludes axial movement of flange portions 242 and 274. Bottom seal collar 246 is positioned within a central portion of the chamber defined by housing 216 in a manner that permits it to move or float toward and away from top seal collar 248. Such movement is effective to elongate or stretch the seal member 234 and thereby increase the inner diameter of the center bore portion 240.

The axial movement of the bottom seal collar 246 is controlled by the seal expander member 250. Member 250 is a generally rectangular member having a rectangular opening 254 formed therein. A pair of opposing fingers 256 extend outwardly from end portions 257 of member 250. The expander member is positioned in housing 216 with the seal member 234 and cage member 270 extending through opening 254 and the fingers 256 extending through cooperating openings in housing 216. The expander member is formed with living hinge portions 258, 259 and 260 so that squeezing of fingers 256 towards each other causes a center portion 262 to deflect downwardly and apply a force against the top surface of bottom seal collar 246 and further separate it from top seal collar 248.

Top retainer member 252 is attached to the upper end of housing 216 and is provided with openings to receive suitable attachment means associated with the obturator handle 232. As is well known in the art, trocar assembly 210 includes a flapper valve assembly 264 that is located in housing 216 immediately below bottom collar member 246.

In operation, the trocar assembly 210 is typically received in a form wherein the seal member 234 is in its unstressed condition and wherein the center bore portion 240 has an inner diameter of about 4.0 mm. In this condition, the seal member 234 is able to seal against implements having outer diameters from about 5.0 mm to about 12.0 mm. When it is necessary to direct an implement having sharp tips spaced greater than about 6.0 mm through the trocar assembly 210, fingers 256 are squeezed toward each other causing the center portion 262 of seal expander member 250 to deflect downwardly. The downward movement of portion 262 causes bottom seal collar 246 to further separate from top seal collar 248 and thereby elongate or stretch seal member 234. The elongation of seal member 234 causes the inner diameter of center bore 240 to increase and thereby facilitate the insertion of larger diameter implements therethrough. The floating of bottom seal collar 246 compensates for non-concentrically located implements in a similar manner as discussed above with respect to the embodiment shown in FIGS. 1-3.

Referring to FIG. 10, there is shown a seal member 334 having a unique cross-sectional configuration in accordance with the invention. It is anticipated that the above described seal members 34, 134 and 234 may be formed With the same cross-sectional configuration as seal member 334. Seal member 334 has converging and diverging side walls 336 and 338 that form a constricted center bore portion 340 at the intersection thereof. The outer edges of side walls 336 and 338 are respectively formed with flange portions 342 and 344. The center bore portion 340 has a reduced thickness to facilitate insertion and extraction of implements therethrough. The thickness of the side walls 336 and 338 decreases as they extend toward the center bore portion. In accordance with a preferred embodiment of the invention the center bore portion has a thickness of approximately 0.015 inches and the thickness of the side walls increases to about 0.04 inches.

Figure 17:
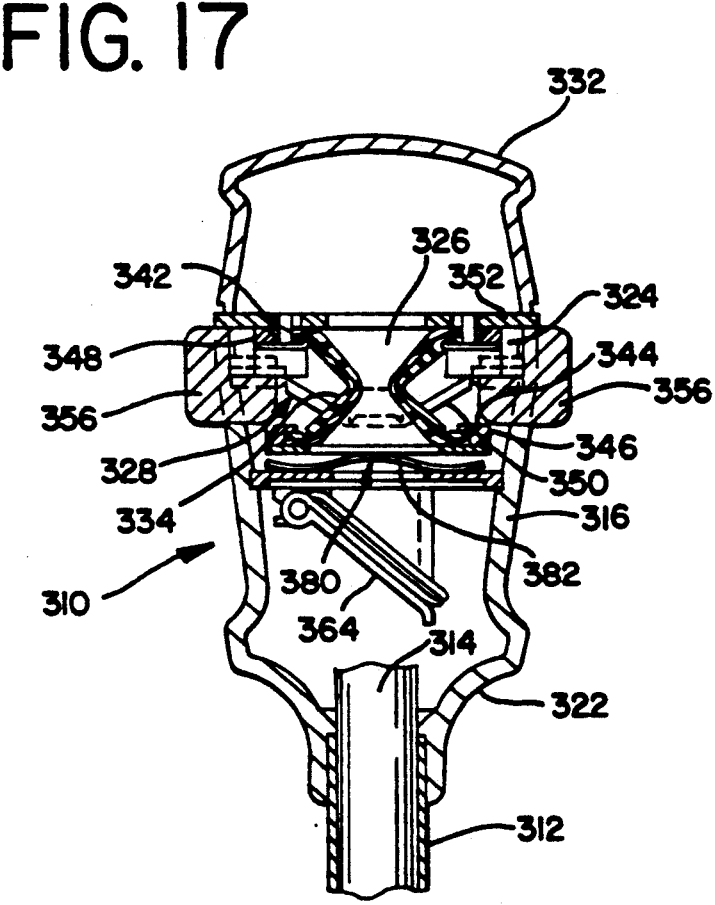
FIG. 17 is a cross-sectional view similar to FIG. 13 of a fourth preferred embodiment of a trocar assembly device incorporating a seal member assembly constructed in accordance with the invention.

Referring to FIG. 17, there is disclosed a fourth preferred embodiment of a trocar assembly device 310 that is similar in construction to the trocar assembly 210 shown in FIGS. 11-13 and described above. In order to facilitate the disclosure of trocar assembly 310, the elements in this device which are common to the elements in trocar assembly 210 are identified with the same reference numeral as used to identify such element in trocar assembly 210 plus 100. That is, element 210 in FIG. 13 corresponds to element 310 in FIG. 17. The discussion of the common elements above is herein incorporated by reference.

The only structural difference between the trocar assembly 210 and trocar assembly 310 is that trocar assembly 310 is provided with a biasing means 380 to apply an upward biasing force to the bottom seal collar 346. The biasing force compresses seal member 334 and causes a reduction in the diameter of the center bore portion 340. As with respect to trocar assembly 210, squeezing of fingers 356 toward each other causes the seal member 334 to elongate against the bias of the biasing means, and thereby increase the inner diameter of center bore portion 340. In accordance with a preferred embodiment, biasing means 380 includes a leaf spring member 382 that is positioned between bottom collar 346 and flapper valve assembly 364.

The operation of trocar assembly 310 in most respects is the same as the operation of trocar assembly 210 discussed above. However, center bore portion 340 of the seal member 334 when in its relaxed state prior to exertion of external forces has an inner diameter of preferably from about 5.0 mm to about 8.0 mm. The biasing means 380 causes the seal member to axially compress and thereby reduces the inner diameter of center bore portion 340 to preferably from about 1.0 mm to about 3.0 mm. The squeezing of fingers 356 toward each other causes the seal member to elongate and thereby increases the inner diameter of center bore portion 340 as discussed above.

From the foregoing it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modifications as fall within the scope of the claims.

What is claimed is:
1. A trocar assembly for providing communication into an anatomical cavity, comprising:
 (a) a trocar tube defining an interior lumen having an open distal end portion and an open proximal end portion for accommodating axial reciprocation of an elongate implement of lesser cross-sectional dimension therethrough;
 (b) means adjoining said proximal end portion of said trocar tube defining a chamber having open distal and proximal end portions that communicate with said lumen and permit axial reciprocation of an elongate implement therethrough;

(c) seal means positioned in said chamber, said seal means defining a constricted center bore portion allowing an elongate implement to pass therethrough in sealing engagement therewith, said seal means sealing said proximal end portion of said chamber, said seal means has a generally hourglass shape defining generally converging and diverging side walls that form said constructed center bore portion at the intersection thereof; and (d) expanding means for enlarging said center bore portion so as to increase the inner diameter thereof, said expanding means deflects said seal means in an axial direction.

2. The trocar assembly as defined in claim 1 wherein the ratio of the axial deflection of said seal means to the change in diameter of said center bore portion is from about 1:3 to about 3:1.

3. The trocar assembly as defined in claim 2 wherein the ratio of the axial deflection of said seal means to the change in diameter of said center bore portion is about 1:1.

4. The trocar assembly as defined in claim 2 wherein said converging and diverging side walls of said seal means have spaced apart axially extending tensile elements formed therein.

5. The trocar assembly as defined in claim 4 wherein said tensile elements are tension bearing elements that do not sustain compressive loads.

6. The trocar assembly as defined in claim 4 wherein from about 3 to about 12 tensile elements are provided in said side walls.

7. The trocar assembly as defined in claim 1 wherein said seal means includes an inner end portion and an outer end portion, and said expanding means retains either said inner end portion or said outer end portion in a fixed position and causes the other end portion to float and further separate from the fixed end portion.

8. The trocar assembly as defined in claim 7 wherein said expanding means includes a bottom seal collar secured to said inner end portion of said seal means, said bottom seal collar being secured within said chamber to preclude axial movement of said inner end portion.

9. The trocar assembly as defined in claim 8 wherein said expanding means includes an expander member positioned within said chamber, said expander member having an opening formed therein for receipt of said seal means therethrough, said expander member having a center portion positioned between a pair of end portions, said center portion applying a force to said outer portion of said seal means to cause said outer portion to further separate from said inner portion of said seal means and enlarge the center bore portion of said seal means.

10. The trocar assembly as defined in claim 9 wherein said expander member has living hinge portions formed therein that separate said center portion from said end portions of said expander member such that application of a squeezing force to said end portions of said expander member causes said center portion to deflect upwardly and apply said force to said outer portion of said seal means.

11. The trocar assembly as defined in claim 10 wherein said expander member includes fingers that extend from said end portions of said expander member, said fingers extend through openings in said chamber such that application of a squeezing force to said fingers causes said center portion to deflect upwardly.

12. The trocar assembly as defined in claim 9 wherein said expanding means includes a top seal collar secured to said outer end portion of said seal means, said top seal collar being positioned in said chamber to permit axial movement of said outer end portion.

13. The trocar assembly as defined in claim 7 wherein said expanding means includes a top seal collar secured to said outer end portion of said seal means, said top seal collar being secured within said seal means to preclude axial movement of said outer end portion.

14. The trocar assembly as defined in claim 13 wherein said expanding means includes an expander member positioned within said chamber, said expander member having an opening formed therein for receipt of said seal means therethrough, said expander member having a center portion positioned between a pair of end portions, said center portion applying a force to said inner portion of said seal means to cause it to further separate from said outer portion of said seal means and enlarge the center bore portion of said seal means.

15. The trocar assembly as defined in claim 14 wherein said expander member has living hinge portions formed therein that separate said center portion from said end portions of said expander member such that application of a squeezing force to said end portions of said expander member causes said center portion to deflect downwardly and apply said force to said inner portion of said seal means.

16. The trocar assembly as defined in claim 15 wherein said expander member includes fingers that extend from said end portions of said expander member, said fingers extend through openings in said chamber such that application of a squeezing force to said fingers causes said center portion to deflect downwardly.

17. The trocar assembly as defined in claim 14 wherein said expanding means includes a bottom seal collar secured to said inner end portion of said seal means, said bottom seal collar being positioned in said chamber to permit axial movement of said inner end portion.

18. The trocar assembly as defined in claim 1 wherein said seal means has a reduced thickness at said constricted center bore portion.

19. The trocar assembly as defined in claim 1 wherein the thickness of said converging and diverging side walls decreases as they extend toward said center bore portion.

20. The trocar assembly as defined in claim 1 wherein said seal means includes an annular flange extending outwardly from the peripheral edges of said converging and diverging side walls.

21. The trocar assembly as defined in claim 2 wherein said seal means is received within a cage member defining a plurality of spaced apart axially extending rib portions that are positioned adjacent said converging and diverging sidewalls.

22. The trocar assembly as defined in claim 21 wherein said cage member is integrally molded to said seal means.

23. The trocar assembly as defined in claim 21 wherein said rib portions are formed with a living hinge at an intermediate portion thereof adjacent said center bore portion.

24. The trocar assembly as defined in claim 7 further including biasing means for biasing said other end portion toward said fixed end portion so as to reduce the inner diameter of said center bore portion.

25. The trocar assembly as defined in claim 24 wherein said biasing means is a spring means positioned adjacent said other end portion.

26. The trocar assembly as defined in claim 17 further including a spring means positioned adjacent said bottom seal collar for biasing inner end portion toward said outer end portion so as to reduce the inner diameter of said center bore portion.

* * * * *